United States Patent

McGee

(10) Patent No.: US 7,490,604 B2
(45) Date of Patent: Feb. 17, 2009

(54) ENDOTRACHEAL SURFACTANT DISTRIBUTION SYSTEM

(75) Inventor: Thomas E. McGee, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 10/391,172

(22) Filed: Mar. 17, 2003

(65) Prior Publication Data

US 2004/0007236 A1  Jan. 15, 2004

Related U.S. Application Data

(60) Provisional application No. 60/364,506, filed on Mar. 15, 2002.

(51) Int. Cl.
  *A61M 16/00* (2006.01)
  *A62B 9/04* (2006.01)

(52) U.S. Cl. .................... 128/200.26; 128/207.14; 128/202.27

(58) Field of Classification Search ............ 128/207.14, 128/207.16, 200.26, 204.18, 205.24, 911, 128/912, 202.27, 207.15; 604/27, 32, 35, 604/30
See application file for complete search history.

(56) References Cited

U.S. PATENT DOCUMENTS

| | | | | |
|---|---|---|---|---|
| 4,834,726 A | * | 5/1989 | Lambert | 604/540 |
| 4,836,199 A | * | 6/1989 | Palmer | 128/207.16 |
| 4,850,350 A | * | 7/1989 | Jackson | 128/207.16 |
| 5,025,806 A | * | 6/1991 | Palmer et al. | 128/203.12 |
| 5,029,580 A | * | 7/1991 | Radford et al. | 128/207.14 |
| 5,060,646 A | * | 10/1991 | Page | 128/207.14 |
| 5,065,754 A | * | 11/1991 | Jensen | 128/200.26 |
| 5,083,561 A | * | 1/1992 | Russo | 128/207.16 |
| 5,125,893 A | * | 6/1992 | Dryden | 604/500 |
| 5,269,756 A | * | 12/1993 | Dryden | 604/171 |
| 5,309,902 A | * | 5/1994 | Kee et al. | 128/202.27 |
| 5,309,903 A | * | 5/1994 | Long | 128/203.12 |
| 5,325,851 A | * | 7/1994 | Reynolds et al. | 128/207.16 |
| 5,343,857 A | * | 9/1994 | Schneider et al. | 128/202.27 |
| 5,354,267 A | * | 10/1994 | Niermann et al. | 604/32 |
| 5,355,876 A | * | 10/1994 | Brodsky et al. | 128/202.27 |
| 5,357,946 A | * | 10/1994 | Kee et al. | 128/200.24 |
| 5,368,017 A | * | 11/1994 | Sorenson et al. | 128/200.26 |
| 5,433,195 A | * | 7/1995 | Kee et al. | 128/207.14 |
| 5,490,503 A | * | 2/1996 | Hollister | 128/205.12 |
| 5,598,840 A | * | 2/1997 | Iund et al. | 128/207.14 |
| 5,628,306 A | * | 5/1997 | Kee | 128/203.12 |
| 5,694,922 A | * | 12/1997 | Palmer | 128/202.27 |

(Continued)

*Primary Examiner*—Teena Mitchell
(74) *Attorney, Agent, or Firm*—Holland & Hart

(57) ABSTRACT

Apparatus for delivering a medicament through an artificial airway connected to a patient ventilation/aspiration system without breaking the ventilation circuit comprises a manifold with an interior chamber communicating with first, second and third ports. The manifold is structured and arranged to maintain an uninterrupted ventilation pathway between the first and second ports and to provide a travel path for a suction catheter between the second and third ports, the second port being adapted for connection to the artificial airway. The apparatus further includes a catheter assembly, including a catheter with a lumen, positioned within a protective sleeve and slidable through a distal end fixture connected to the third port. The catheter assembly is structured and arranged to permit advancement of the distal end of the catheter through the manifold and artificial airway. A syringe and a suction control valve are interchangeably connectable to the proximal end of the catheter assembly.

20 Claims, 2 Drawing Sheets

U.S. PATENT DOCUMENTS

| | | | | |
|---|---|---|---|---|
| 5,711,294 A * | 1/1998 | Kee et al. | | 128/202.27 |
| 5,730,123 A * | 3/1998 | Lorenzen et al. | | 128/207.14 |
| 5,738,091 A * | 4/1998 | Kee et al. | | 128/205.12 |
| 5,775,325 A * | 7/1998 | Russo | | 128/205.12 |
| 5,803,078 A * | 9/1998 | Brauner | | 128/207.14 |
| 5,882,348 A * | 3/1999 | Winterton et al. | | 604/537 |
| 5,919,174 A * | 7/1999 | Hanson | | 604/533 |
| 6,012,451 A * | 1/2000 | Palmer | | 128/200.26 |
| 6,013,619 A * | 1/2000 | Cochrane et al. | | 514/2 |
| 6,318,368 B1 * | 11/2001 | Morejon | | 128/207.15 |
| 6,494,203 B1 * | 12/2002 | Palmer | | 128/202.27 |
| 6,543,451 B1 * | 4/2003 | Crump et al. | | 128/207.14 |
| 6,729,326 B1 * | 5/2004 | Winterton et al. | | 128/203.12 |

* cited by examiner

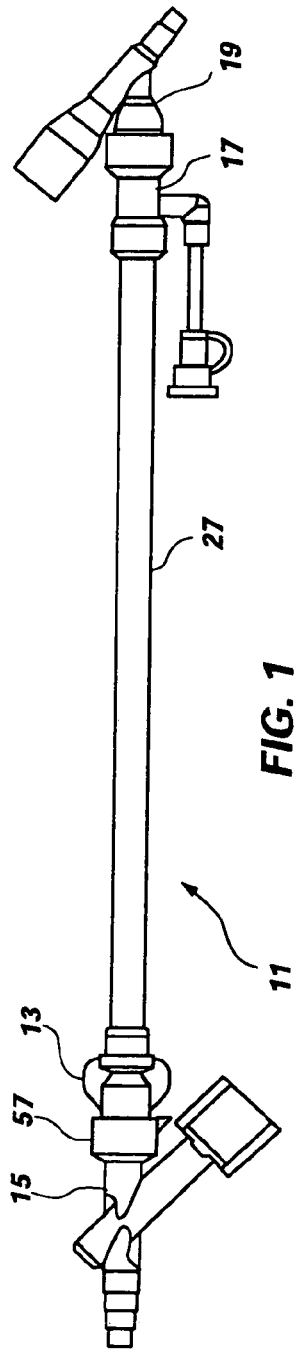
FIG. 1
–Prior Art–
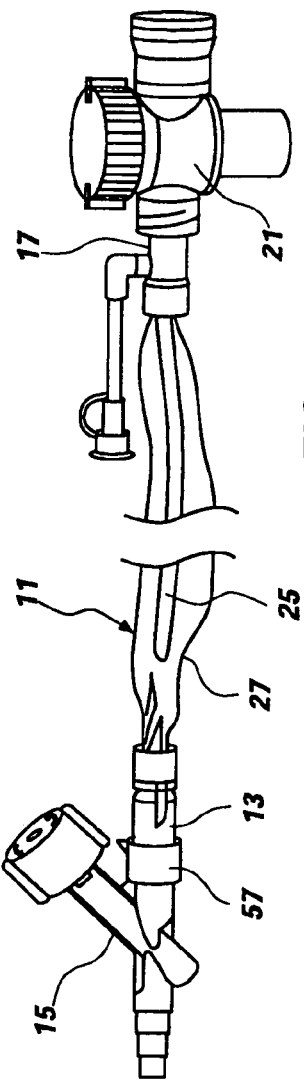
FIG. 2
–Prior Art–
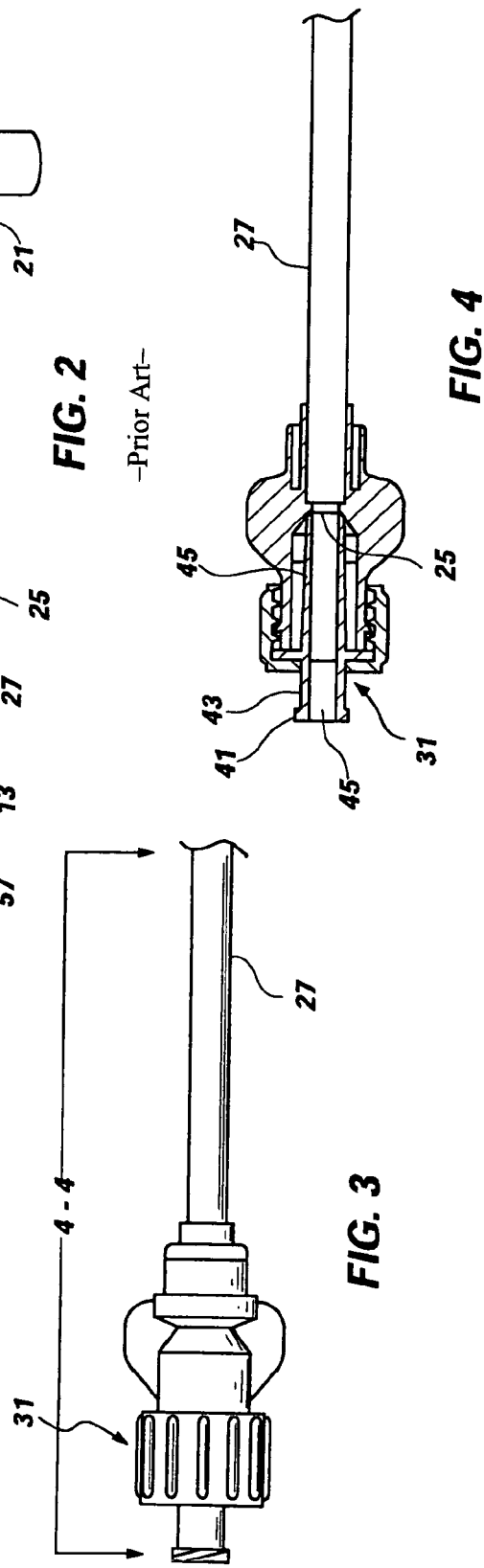
FIG. 3
FIG. 4

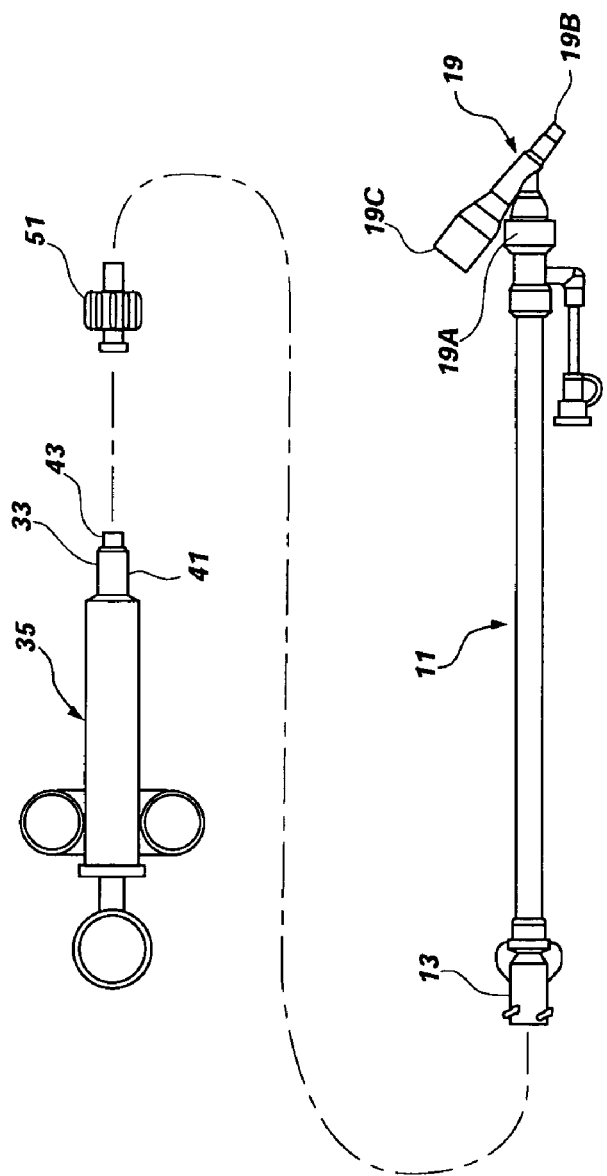
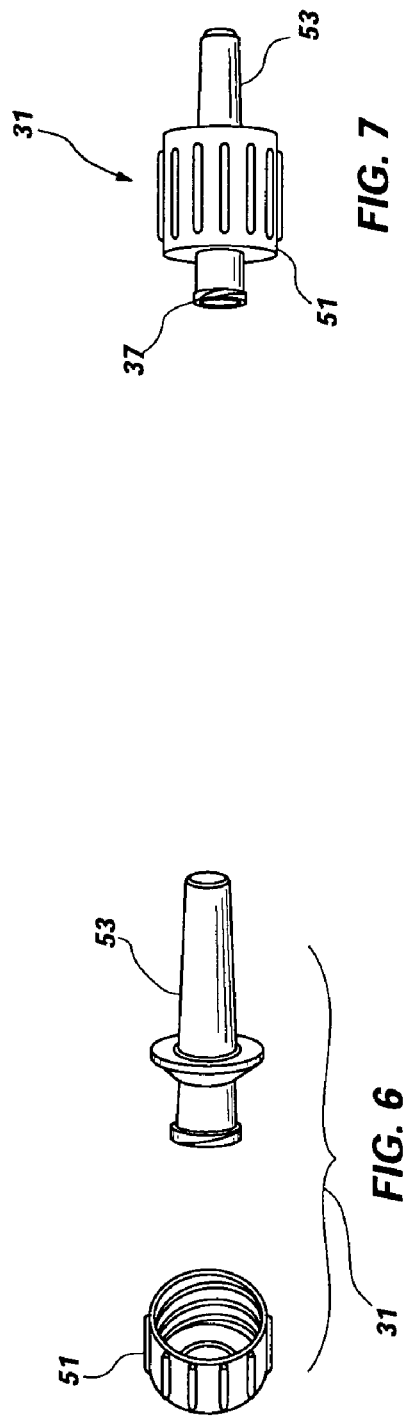

ENDOTRACHEAL SURFACTANT DISTRIBUTION SYSTEM

PRIORITY CLAIM

This application claims the benefit of the Mar. 15, 2002, filing date of provisional patent application 60/364,506, entitled "Endotracheal Surfactant Distribution System."

BACKGROUND OF THE INVENTION

1. Field

This invention relates generally to endotracheal procedures and is specifically directed to the delivery of surfactant to lung tissues in connection with such procedures. It provides a system which permits the delivery of surfactant through an artificial airway of an endotracheal ventilation/aspiration system without interrupting ventilation.

2. State of the Art

Many gas delivery systems, particularly in a hospital or laboratory environment, utilize manifold devices for directing fluid flow. There is a variety of circumstances in which it is necessary or desirable to provide multiple, yet isolated, other pathways through the interior of such a manifold. The manifold is often associated with other components as a system. When the individual components of such a system are subjected to mechanical forces tending to rotate one component with respect to another, it is often desirable to provide that travel path through a joint structure which permits rotating or swiveling movement.

As an example, closed systems for endotracheal suctioning and ventilating typically include a manifold structured to enable the introduction of ventilating gases and intermittent exhalation of patient breath simultaneously with insertion and operation of a tracheal suctioning catheter. The manifold structure typically includes multiple ports, usually the open ends of respective conduits extending from a common chamber. One such port is interfaced to a patient through a patient connection device, which in turn provides access to an artificial airway positioned within the patient by a predicate intubation procedure. The suction catheter is often included within an assembly, which is connectable to a second port of the manifold. The catheter assembly conventionally includes a collapsible plastic envelope positioned to entirely surround the catheter. A practitioner manually externally collapses the envelope onto the external surface of the catheter and advances the catheter through the manifold into an access tube connected to a patient, retracting the catheter in a similar fashion following the aspiration procedure.

The manifold thus provides a first pathway for ventilation gases and a second pathway for the catheter. The catheter provides isolation from the ventilating gases for fluids withdrawn from the patient through the manifold. When the catheter is withdrawn, it is often desired to continue regulated ventilation through the manifold. In some cases, it is desirable for the catheter assembly to be disconnected from the manifold without disturbing the ventilation of the patient. Certain manifold assemblies are thus structured to provide for a gastight sealing of the pathway formerly occupied by the catheter upon its removal.

Material prior art structures and methods are described, among other places, in U.S. Pat. No. 5,333,607 to Kee, et al.; U.S. Pat. No. 5,354,267 to Niermann, et al.; U.S. Pat. Nos. 5,357,946 and 5,445,141 to Kee, et al.; U.S. Pat. Nos. 5,140, 983 and 5,487,381 to Jinotti; U.S. Pat. No. 5,882,348 to Winterton et al.; U.S. Pat. Nos. 5,735,271 and 5,730,123 to Lorenzen et al. and U.S. Pat. No. 5,642,726 to Owens et al.

These patents each disclose ventilator manifold devices (some of which are assemblies of components) and systems with which those devices are utilized. The '267 patent, for example, discloses an assembly including a manifold and an associated multiposition stop cock valve. The valve is provided with a "Tee"-shaped internal stem channel pattern so that the stem may be positioned selectively to wash the internal lumen of a catheter to irrigate the patient or to accommodate travel of the catheter through the stem to suction the patient. The valve may be plugged directly into an access port of the manifold. Patient ventilation is conducted without respect to the valve through other ports of the manifold. The valve itself constitutes an integral component of a catheter assembly and must be removed from the remainder of the manifold with the remainder of that assembly. The '348 patent discloses a valved manifold embodying a multiposition stop cock valve. This manifold may be integral with a catheter assembly, but is alternatively structured to be detachable from the catheter assembly. The ventilation port is transverse the patient interface port and is, thus, characterized by more dead airspace than is generally regarded as acceptable for neonatal applications.

The disclosure of commonly assigned, copending U.S. patent application Ser. No. 09/723,011, filed Nov. 27, 2000, entitled "NEONATAL VALVED MANIFOLD," is hereby incorporated herein by reference. Ser. No. 723,011 discloses a manifold assembly incorporating a valve constructed and arranged to minimize dead airspace within the manifold, while remaining capable of passing a catheter. The disclosed valve provides a sealed gas flow path through the manifold in both its open and closed conditions with respect to catheter travel. The manifold may be constructed as either integral with or detachable from any associated catheter assembly. It includes a ventilation port that is substantially axially aligned with the patient interface port and is constructed to minimize fluid flow turbulence of ventilating gases, among other features particularly advantageous to neonatal applications.

Neonatal endotracheal procedures present a number of special problems. Of particular interest to this invention is the low level of surfactant naturally present in neonatal lung tissues. Endotracheal procedures that are routinely performed on juveniles or adults are impracticable to apply to neonatal tissues without taking steps to compensate for these low surfactant levels. It has become an accepted procedure to introduce surfactant (usually obtained from bovine or equine lung tissue) to the proximity of neonatal lung tissue prior to commencing suctioning procedures. Surfactant has typically been introduced by injection from a syringe through the artificial airway that is inevitably present following a conventional intubation procedure. Because of the tendency for injected surfactant to become entrapped within the artificial airway, however, more recent techniques involve the injection of surfactant through a catheter inserted down the artificial airway to beyond its termination. Discharge of the surfactant beyond the artificial airway ensures actual delivery of the surfactant to lung tissue and avoids the potential for blow back of surfactant during subsequent ventilation. A feeding tube (typically a 5F size) has conventionally been used for this purpose, with the ventilation circuit absent from the artificial airway. More recently, special catheters, such as the multiple access catheter (MAC) marketed by the Ballard Medical Products subsidiary of Kimberly-Clark Health Care of Roswell, Ga., under the marks "KIMBERLY CLARK BALLARD" and "TRACH CARE" have been offered as a means for maintaining PEEP and Oxygen levels during surfactant delivery. Use of these delivery systems inevitably requires breaking the ventilation circuit, however, to exchange the surfactant and suction catheters required for the complete endotracheal procedure. A need thus remains for an improved surfactant delivery method and apparatus which avoids the interruption of ventilation.

SUMMARY OF THE INVENTION

The invention may be regarded as an improved surfactant delivery system which enables a novel method for introducing surfactant (or other medicaments) to the proximity of lung tissue. The system relies upon a novel arrangement of components, together constituting an endotracheal ventilation/aspiration assembly. The principal innovation of the system, and of the assembly, is an adaptor element, which interfaces a syringe to the proximal (near the technician, but remote from the patient) end of a suction catheter. Accordingly, surfactant may be delivered to the desired site through the same catheter that will subsequently function as the suction catheter. A surfactant delivery episode can thus be accomplished without interrupting the ventilation circuit. The need for exchanging catheters during the procedure is eliminated.

This disclosure focuses upon the special case of surfactant delivery to neonatal lung tissue. It should be understood, however, that the system may readily be used to deliver any fluid which is deemed appropriate to inject through the suction catheter of an endotracheal catheter assembly while maintaining ventilation capability. Similarly, surfactant may be delivered to juvenile or adult lung tissue by this means, although the desirability of doing so occurs much less frequently. From an apparatus standpoint, the syringe adaptor component of this invention provides greater versatility to an endotracheal assembly than has heretofore been available. Moreover, while this disclosure describes the invention with reference to a syringe delivery device, other storage and delivery devices may be interfaced with the proximal end of a catheter in similar fashion.

The delivery method of this invention begins with a conventional intubation procedure, which establishes an artificial airway through the trachea of a patient (typically, a neonatal patient) to the treatment site (typically, adjacent lung tissue). A manifold with an interior chamber communicating with first, second and third ports, structured and arranged to maintain a travel path for a suction catheter between the first and second ports and an uninterrupted ventilation pathway between the second and third ports, is connected to the entry of the artificial airway in conventional fashion. A valved manifold, of the type disclosed, for example, by U.S. Pat. No. 5,354,267 or U.S. Pat. No. 5,882,348 or the aforementioned Ser. No. 09/723,011, is generally preferred, as contributing more versatility to the assembly. The function of the valved manifold of interest to this invention is to provide for uninterrupted ventilating capability at all stages of the procedure, all as described by the '348 patent. In any case, the manifold is connected at its proximal end to the distal end of a suction catheter assembly. The proximal end of the catheter assembly carries structure that is constructed to interconnect to a vacuum control valve. According to this invention, a storage and delivery component (typically, a syringe) containing a supply of medicament (typically surfactant) is connected to the proximal end of the catheter assembly in place of the vacuum control valve. The manifold valve is opened, and the catheter is advanced through the manifold and down the artificial airway until the distal end of the catheter is in proper position. The syringe may then be operated to discharge surfactant to the lungs. A small amount of surfactant inevitably remains within the catheter lumen. To avoid loss of this relatively expensive material, saline (or other fluid) may be introduced (usually by means of a second syringe) to "chase" (displace) this residual material from the lumen. The syringe may then be decoupled from the proximal end of the catheter assembly and replaced by the conventional vacuum valve. Aspiration can then be implemented in conventional fashion.

BRIEF DESCRIPTION OF THE DRAWINGS

In the drawings, which illustrate what is currently regarded as the best mode for carrying out the invention:

FIG. 1 is a plan view of an endotracheal catheter assembly, which can be used in the practice of this invention;

FIG. 2 is a plan view of an alternative catheter assembly, which can be used in the practice of this invention;

FIG. 3 is a partial plan view illustrating the adaptor component of this invention in association with the proximal end of the catheter component of either of the assemblies illustrated by FIGS. 1 and 2;

FIG. 4 is a cross-sectional view, taken along the section line 4—4 of FIG. 3;

FIG. 5 is an exploded plan view of an assembly of this invention;

FIG. 6 is an exploded pictorial view of a syringe adaptor component of this invention; and FIG. 7 is a pictorial view of an alternative syringe adaptor component of this invention.

DETAILED DESCRIPTION OF THE ILLUSTRATED EMBODIMENT

FIGS. 1 and 2 illustrate alternative equipment sets with which this invention may be practiced. In each case, a catheter assembly, generally 11, is connected at its proximal end to a connector 13, which couples to a suction control valve 15. The distal end of the assembly 11 carries a second connector 17, which couples to a manifold 19, FIG. 1; 21, FIG. 2. As best shown by FIG. 2, the assembly 11 includes a catheter 25 within a protective flexible sleeve 27. The manifold 19 illustrated by FIG. 1 is particularly adapted for neonatal applications, as disclosed more particularly by Ser. No. 09/723,011. The manifold 21 illustrated by FIG. 2 is generally used with the ventilation/aspiration circuits applied to adult and juvenile procedures.

In any case, FIGS. 3–6 illustrate one version of an adaptor 31 which serves to interface the discharge end 33 of a syringe 35, FIG. 5, to the proximal connector 13 in place of the valve 15. Discharge syringe ends 33 are conventionally configured as either "slip type" or "threaded type." The illustrated adaptor 31 carries external threads 37 adapted to mate with complementary internal threads carried by a tubular extension 41 at the discharge end 33. Whether or not the threads 37 are present, a tapered extension 43 registers with a socket 45 within the connector 13. FIG. 7 illustrates the adaptor 31 as a unitary structure, while FIG. 6 illustrates basically the same structure as an assembly of a cap 51 and captured barrel element 53. The cap 51 carries internal threads which mate with complementary external threads of the connector 13, as best illustrated by FIG. 4. Preferably, this threaded connection is of standard Luer Lock construction, thereby being directly interchangeable with the cap portion 57 of the valve 15 (FIG. 1).

The illustrated embodiments are each useful for the practice of various methods involving the delivery of one or more medicaments to a treatment site (not shown) through an artificial airway (not shown) associated with a patient ventilation/aspiration system. The novel portions of the methods of this invention commence after an artificial airway has been established through the trachea of a patient to a treatment site in any conventional fashion. Referring to FIG. 5, an appropriate manifold, such as manifold 19, is then connected to the entry of the artificial airway in conventional fashion. While the manifold may be either customized or standard in design, the method involves providing a manifold having an interior chamber communicating with first port 19A, second port 19B and third port 19C, structured and arranged to maintain a travel path for a suction catheter between the first 19A and second 19B ports and an uninterrupted ventilation pathway between the second 19B and third 19C ports. A catheter assembly 11 is installed in communication with the first port 19A, the proximal end of the catheter assembly 11 carrying connector 13 that is constructed to interconnect to a suction control valve (e.g., 15, FIG. 2). A storage and delivery component, such as syringe 35, containing a supply of medicament is connected through connector 13 to the proximal end of the catheter assembly 11, as shown. In the illustrated instance, a cap 51 is utilized to interface the extension 43 of the syringe 35 to the connector 13. The distal end of a catheter component (25, FIG. 2) of the catheter assembly 11 is advanced through the second port 19B and the artificial airway to the treatment site. The syringe 35 is then operated to discharge medicament to the treatment site. The storage and delivery component (e.g., syringe 35) is removed from the proximal end of the catheter assembly 11 and is replaced by a suction control device (e.g., valve 15). The catheter assembly 11 may then be returned to its conventional functioning as a component of an endotracheal suctioning system. The method is practiced in its entirety without disturbing the assisted ventilation capability of the manifold 19 via ports 19B and 19C.

This invention may be characterized as a method for delivering a medicament to a treatment site through an artificial airway associated with a patient ventilation/aspiration system, comprising: (1) applying an intubation procedure, whereby to establish such an artificial airway through the trachea of a patient to a treatment site, the airway including an entry from outside the patient; (2) connecting to the entry a manifold having an interior chamber communicating with a first, proximal port, a second, distal port and a third port, all structured and arranged to maintain a travel path for a suction catheter between the first and second ports and an uninterrupted ventilation pathway between the second and third ports, the second port being in communication with the artificial airway at the entry; (3) connecting a suction catheter assembly to the first port, the catheter assembly having a proximal end, a distal end connected to the first port and a catheter component, having proximal and distal ends and being insertable through the first port, along the travel path and through the entry; (4) advancing the distal end of the catheter component to the treatment site while maintaining the uninterrupted ventilation pathway between the second and third ports; and (5) introducing medicament into the proximal end of the catheter component, whereby to discharge a quantity of the medicament through the distal end of the catheter component at the treatment site, while maintaining the uninterrupted ventilation pathway between the second and third ports.

Some more specific embodiments include the step of applying suction to the distal end of the catheter component, whereby to implement aspiration, following the introduction of the medicament. Other specific embodiments involve the introduction of medicament into the proximal end of the catheter component by means of a syringe coupled to the proximal end of the catheter component. In some cases, following the introduction of medicament, the syringe is decoupled from the proximal end of the catheter component and a suction control device is selectively coupled to the proximal end of the catheter component to apply suction to the distal end of the catheter component, whereby to implement aspiration.

Importantly, the method may be specifically adapted for the delivery of surfactant to the proximity of lung tissue of a neonatal patient by (1) applying an intubation procedure, whereby to establish an artificial airway through the trachea of the patient to a treatment site proximate the lungs of the patient, the airway including an entry from outside the patient; (2) connecting to the entry a manifold having an interior chamber communicating with a first, proximal port, a second, distal port and a third port, structured and arranged to maintain a travel path for a suction catheter between the first and second ports and an uninterrupted ventilation pathway between the second and third ports, the second port being in communication with the artificial airway at the entry; (3) connecting a suction catheter assembly to the first port, the catheter assembly having a proximal end, a distal end connected to the first port and a catheter component, having proximal and distal ends and being insertable through the first port, along the travel path and through the entry; (4) advancing the distal end of the catheter component to the treatment site while maintaining the uninterrupted ventilation pathway between the second and third ports; and (5) introducing surfactant into the proximal end of the catheter component, whereby to discharge a quantity of the surfactant through the distal end of the catheter component at the treatment site, while maintaining the uninterrupted ventilation pathway between the second and third ports.

Preferred neonatal procedures include the step of applying suction to the distal end of the catheter component, whereby to implement aspiration, following the introduction of the surfactant. It is also preferred practice to introduce surfactant into the proximal end of the catheter component by means of a syringe coupled to the proximal end of the catheter component. Following the introduction of surfactant, the syringe is usually decoupled from the proximal end of the catheter component and a suction control device is coupled to the proximal end of the catheter component selectively to apply suction to the distal end of the catheter element, whereby to implement aspiration, following the introduction of the surfactant. Ideally, after the syringe is decoupled, residual surfactant remaining within the lumen of the catheter component is displaced to the treatment site. The suction control device may then be coupled to the proximal end of the catheter component.

What is claimed is:

1. A method for delivering a medicament to a treatment site through an artificial airway associated with a patient ventilation/aspiration system, comprising:

establishing an artificial airway through the trachea of a patient to a treatment site;

connecting a manifold with an interior chamber communicating with first, second and third ports, structured and arranged to maintain a travel path for a suction catheter between said first and second ports and an uninterrupted ventilation pathway between said second and third ports to an entry of said artificial airway;

providing a catheter assembly in communication with said first port, a proximal end of said catheter assembly carrying structure that is constructed to interconnect to a vacuum control valve;

connecting a storage and delivery component containing a supply of medicament to said proximal end of said catheter assembly;

advancing a catheter of said catheter assembly to said treatment site;

operating said storage and delivery component to discharge medicament through a lumen of said catheter to said treatment site;

removing said storage and delivery component from said proximal end of said catheter assembly; and connecting a suction control device to said proximal end of said catheter assembly to effect suction through the lumen of said catheter through which the medicament is discharged.

2. The method according to claim 1, wherein said storage and delivery component is a syringe with a discharge end removably connectable to said proximal end of said catheter assembly, said medicament is surfactant, and said suction control device is a valve.

3. A method for delivering a medicament to a treatment site through an artificial airway associated with a patient ventilation/aspiration system, comprising:

applying an intubation procedure, to establish such an artificial airway through the trachea of a patient to a treatment site, said artificial airway including an entry from outside the patient;

connecting to said entry a manifold having an interior chamber communicating with a first, proximal port, a second, distal port, and a third port, structured and arranged to maintain a travel path for a suction catheter between said first and second ports and an uninterrupted ventilation pathway between said second and third ports, said second port being in communication with said artificial airway at said entry;

connecting a suction catheter assembly to said first port, said suction catheter assembly having a proximal end, a distal end connected to said first port, and a catheter component, comprising a lumen having proximal and distal ends and being insertable through said first port, along said travel path and through said entry;

advancing said distal end of said lumen of said catheter component to said treatment site while maintaining said uninterrupted ventilation pathway between said second and third ports; and introducing medicament into said proximal end of said lumen of said catheter component, so as to discharge a quantity of medicament through said distal end of said lumen of said catheter component at said treatment site while maintaining said uninterrupted ventilation pathway between said second and third ports; and applying suction to said distal end of said lumen of said catheter component into which said medicament is introduced, so as to implement aspiration, following the introduction of said medicament.

4. The method according to claim 3, wherein medicament is introduced into said proximal end of said lumen of said catheter component by means of a syringe coupled to said proximal end of said lumen of said catheter component.

5. A method for delivering a medicament to a treatment site through an artificial airway associated with a patient ventilation/aspiration system, said method comprising:

applying an intubation procedure, to establish such an artificial airway through the trachea of a patient to a treatment site, said artificial airway including an entry from outside the patient;

connecting to said entry a manifold having an interior chamber communicating with a first, proximal port, a second, distal port, and a third port, structured and arranged to maintain a travel path for a suction catheter between said first and second ports and an uninterrupted ventilation pathway between said second and third ports, said second port being in communication with said artificial airway at said entry;

connecting a suction catheter assembly to said first port, said suction catheter assembly having a proximal end, a distal end connected to said first port, and a catheter component, comprising a lumen having proximal and distal ends and being insertable through said first port, along said travel path and through said entry;

advancing said distal end of said lumen of said catheter component to said treatment site while maintaining said uninterrupted ventilation pathway between said second and third ports;

introducing medicament into said proximal end of said lumen of said catheter component, so as to discharge a quantity of medicament through said distal end of said lumen of said catheter component at said treatment site while maintaining said uninterrupted ventilation pathway between said second and third ports, wherein medicament is introduced into said proximal end of said lumen of said catheter component by means of a syringe coupled to said proximal end of said lumen of said catheter component;

decoupling said syringe from said proximal end of said lumen of said catheter component; and coupling a suction control device to said proximal end of said lumen of said catheter component into which said medicament is introduced to selectively apply suction to said distal end of said lumen of said catheter component, so as to implement aspiration.

6. A method for delivering surfactant to the proximity of lung tissue through an artificial airway associated with a neonatal patient ventilation/aspiration system, said method comprising:

applying an intubation procedure, whereby to establish an artificial airway through the trachea of the patient to a treatment site proximate the lungs of said patient, said artificial airway including an entry from outside said patient;

connecting to said entry a manifold having an interior chamber communicating with a first, proximal port, a second, distal port, and a third port, structured and arranged to maintain a travel path for a suction catheter between said first and second ports and an uninterrupted ventilation pathway between said second and third ports, said second port being in communication with said artificial airway at said entry;

connecting a suction catheter assembly to said first port, said suction catheter assembly having a proximal end, a distal end connected to said first port, and a catheter component, comprising a lumen having proximal and distal ends and being insertable through said first port, along said travel path and through said entry;

advancing said distal end of said lumen of said catheter component to said treatment site while maintaining said uninterrupted ventilation pathway between said second and third ports;

introducing surfactant into said proximal end of said lumen of said catheter component, so as to discharge a quantity of said surfactant through said distal end of said lumen of said catheter component at said treatment site while maintaining said uninterrupted ventilation pathway between said second and third ports; and applying suction to said distal end of said lumen of said catheter component into which said surfactant is introduced, so as to implement aspiration, following the introduction of said surfactant.

7. The method according to claim 6, wherein surfactant is introduced into said proximal end of said lumen of said catheter component by means of a syringe coupled to said proximal end of said catheter component.

8. A method for delivering surfactant to the proximity of lung tissue through an artificial airway associated with a neonatal patient ventilation/aspiration system, said method comprising:
applying an intubation procedure, to establish an artificial airway through the trachea of the patient to a treatment site proximate the lungs of said patient, said artificial airway including an entry from outside said patient;
connecting to said entry a manifold having an interior chamber communicating with a first, proximal port, a second, distal port, and a third port, structured and arranged to maintain a travel path for a suction catheter between said first and second ports and an uninterrupted ventilation pathway between said second and third ports, said second port being in communication with said artificial airway at said entry;
connecting a suction catheter assembly to said first port, said suction catheter assembly having a proximal end, a distal end connected to said first port, and a catheter component, comprising a lumen having proximal and distal ends and being insertable through said first port, along said travel path and through said entry;
advancing said distal end of said lumen of said catheter component to said treatment site while maintaining said uninterrupted ventilation pathway between said second and third ports;
introducing surfactant into said proximal end of said lumen of said catheter component, so as to discharge a quantity of said surfactant through said distal end of said lumen of said catheter component at said treatment site while maintaining said uninterrupted ventilation pathway between said second and third ports, wherein surfactant is introduced into said proximal end of said lumen of said catheter component by means of a syringe coupled to said proximal end of said lumen of said catheter component;
decoupling said syringe from said proximal end of said lumen of said catheter component; and
coupling a suction control device to said proximal end of said lumen of said catheter component into which said surfactant is introduced to selectively apply suction to said distal end of said lumen of said catheter component, so as to implement aspiration.

9. The method according to claim 8, wherein following said introducing of surfactant, said syringe is decoupled from said proximal end of said lumen of said catheter component selectively to apply suction to said distal end of said lumen of said catheter component, whereby to implement aspiration, following the introduction of said surfactant.

10. A method for delivering surfactant to the proximity of lung tissue through an artificial airway associated with a neonatal patient ventilation/aspiration system, said method comprising:
applying an intubation procedure to establish an artificial airway through the trachea of the patient to a treatment site proximate the lungs of said patient, said artificial airway including an entry from outside said patient;
connecting to said entry a manifold having an interior chamber communicating with a first, proximal port, a second, distal port, and a third port, structured and arranged to maintain a travel path for a suction catheter between said first and second ports and an uninterrupted ventilation pathway between said second and third ports, said second port being in communication with said artificial airway at said entry;
connecting a suction catheter assembly to said first port, said suction catheter assembly having a proximal end, a distal end connected to said first port, and a catheter component, comprising a lumen having proximal and distal ends and being insertable through said first port, along said travel path and through said entry;
advancing said distal end of said lumen of said catheter component to said treatment site while maintaining said uninterrupted ventilation pathway between said second and third ports; and
introducing surfactant into said proximal end of said lumen of said catheter component, so as to discharge a quantity of said surfactant through said distal end of said lumen of said catheter component at said treatment site while maintaining said uninterrupted ventilation pathway between said second and third ports, wherein surfactant is introduced into said proximal end of said lumen of said catheter component by means of a syringe coupled to said proximal end of said lumen of said catheter component;
decoupling said syringe from said proximal end of said lumen of said catheter component and displacing surfactant remaining within said lumen of said catheter component to said treatment site; and
coupling a suction control device to said proximal end of said lumen of said catheter component into which said surfactant is introduced to selectively apply suction to said distal end of said lumen of said catheter component, so as to implement aspiration, following the introduction of said surfactant.

11. A method of administering a medicament to a treatment site through an artificial airway associated with a patient ventilation/aspiration system, comprising first delivering a medicament to the patient through a lumen of a catheter extending within the artificial airway, then implementing aspiration through the lumen of the catheter through which the medicament is delivered.

12. A method of administering a surfactant to a treatment site through an artificial airway associated with a patient ventilation/aspiration system, comprising first delivering a surfactant to the patient through a lumen of a catheter extending within the artificial airway, then implementing aspiration through the lumen of the catheter through which the surfactant is delivered.

13. A method of delivering medicament comprising:
establishing an artificial airway in a patient;
positioning a catheter comprising a lumen within the artificial airway;
delivering a medicament through the lumen of the catheter;
implementing aspiration using the lumen of the catheter through which the medicament is delivered.

14. The method according to claim 13, wherein the medicament comprises a surfactant.

15. The method according to claim 13, wherein delivering the medicament through the lumen of the catheter assembly comprises:
coupling a syringe containing the medicament to a proximal end of the catheter;
discharging the medicament in the syringe into the lumen of the catheter.

16. The method according to claim 13, wherein the medicament delivered through the lumen of the catheter is delivered proximate to lung tissue of a neonatal patient.

17. The method according to claim 13, wherein positioning the catheter within the artificial airway comprises positioning the catheter beyond a termination point of the artificial airway.

18. The method according to claim 13, wherein implementing aspiration comprises:
coupling a suction control device to a proximal end of the catheter;
selectively applying suction to the first lumen of the catheter using the suction control device.

19. The method according to claim 13, wherein delivering medicament occurs prior to implementing aspiration.

20. The method according to claim 19, wherein implementing aspiration removes medicament from the patient.

* * * * *